United States Patent [19]

Zaidman et al.

[11] 4,217,311

[45] Aug. 12, 1980

[54] METHOD OF PREPARING VINYL CHLORIDE

[76] Inventors: Oleg A. Zaidman, ulitsa Moldagulovoi, 28, korpus 4, kv. 129; Erik V. Sonin, ulitsa Planernaya, 12, korpus 3, kv. 143; Ljudmila B. Sevostianova, ulitsa Gorkogo, 44, kv. 17; Alla N. Melnik, ulitsa Metallurgov, 7/18, kv. 37; Jury A. Treger, ulitsa Bolshaya Cherkizovskaya, 12, korpus 1, kv. 81; Larisa E. Paschenko, ulitsa Sormovskaya, 10, korpus 1, kv. 132; Leonid A. Oshin, ulitsa Textilschikov, 3, kv. 107; Oleg V. Polozov, Sumskoi proezd, 2, korpus 1, kv. 323, all of Moscow, U.S.S.R.

[21] Appl. No.: 965,624

[22] Filed: Dec. 1, 1978

[51] Int. Cl.$^2$ ............................................. C07C 17/02
[52] U.S. Cl. ................................................. 260/656 R
[58] Field of Search .................................... 260/656 R

[56] References Cited

U.S. PATENT DOCUMENTS

| | | | |
|---|---|---|---|
| 2,628,259 | 2/1953 | Dirstine et al. | 260/656 R |
| 3,923,913 | 12/1975 | Antonini et al. | 260/656 R |

*Primary Examiner*—Arthur P. Demers
*Attorney, Agent, or Firm*—Ladas, Parry, Von Gehr, Goldsmith & Deschamps

[57] ABSTRACT

Vinyl chloride is prepared by gas-phase chlorination of a gaseous mixture containing 5 to 50 vol. % of ethane and 50 to 95 vol. % of ethylene. The amount of chlorine supplied into the reaction zone is determined by the formula: number of chlorine moles = $3m + 0.3n$, wherein m is the number of moles of ethane and n is the number of moles of ethylene. Chlorine is supplied into at 4 to 6 points of the reaction zone.

The method of the present invention makes it possible to increase the yield of vinyl chloride up to 70% by weight, while reducing power consumption for the process 1.5 times as compared to the prior art methods.

5 Claims, No Drawings

METHOD OF PREPARING VINYL CHLORIDE

FIELD OF THE INVENTION

The present invention relates to methods of preparing vinyl chloride by way of gas-phase thermal chlorination of ethane and mixtures thereof with other hydrocarbons.

Vinyl chloride is one of the most widely produced monomers in the industry of basic organic synthesis, and the polymers produced therefrom are extensively used in different industries. At present, vinyl chloride is prepared on the basis of ethylene and acetylene. However, due to a rather high cost of the starting components, efforts have been made to prepare vinyl chloride from cheaper and more readily available sources of raw materials. Thus, it is possible to prepare vinyl chloride directly from ethane which is 3–4 times as cheap as ethylene; furthermore, the resources of ethane are substantially limitless. Processing of ethane to vinylchloride may be performed by various methods such as oxychlorination or chlorination on a catalyst. However, the simplest process comprises gas-phase high-temperature chlorination of ethane.

BACKGROUND OF THE INVENTION

Known in the art are methods of preparing ethane chloroderivatives, e.g. vinyl chloride, by way of gas-phase thermal chlorination of ethane. Thus, there is known a method of preparing vinyl chloride, vinylidene chloride and 1,1,1-trichloroethane (methyl chloroform) by chlorination of ethane at a temperature within the range of from 345° to 440° C. under pressure and at a molar ratio of chlorine to ethane equal to 1.5–3:1. Chlorine is supplied at one point of the reaction zone (cf. U.S. Pat. No. 3,304,337).

Due to the pronounced exothermal natura and high speed of the reaction, a great amount of heat is evolved in the chlorination of ethane. Inadequate removal of heat from the reaction zone causes undesirable side processes of resinification and carbon-black formation and, in extreme cases, even explosions. For this reason, one of the main problems associated with the process of gas-phase chlorination of ethane (or mixtures thereof with other hydrocarbons) resides in the provision of the possibility of heat removal from the reaction zone. According to U.S. Pat. No. 3,304,337, heat removal is effected by way of recycling of a portion of the liquid products, i.e. chloroethyl, 1,1-dichloroethane, methylchloroform, into the reaction zone. Therewith, the reaction heat is partially consumed in evaporation of liquid chloroethanes and partially in the endothermal reaction of dehydrochlorination of the same chloroethanes with the formation of unsaturated compounds and hydrogen chloride.

To maintain the process under adiabatic conditions, it is necessary to convert a portion of the resulting vinyl chloride by way of liquid-phase hydrochlorination to 1,1-dichloroethane which is recycled to the reactor.

In accordance with this process, the yield of vinyl chloride does not exceed 35% by weight at a substantially complete conversion of ethane and chlorine.

Also known in the art is a method of preparing vinyl chloride and vinylidene chloride by way of gas-phase thermal chlorination of an ethane-ethylene mixture containing at most 50 mol.% of ethylene (cf. U.S. Pat. No. 2,628,259).

Chlorination of ethane or an ethane-ethylene mixture is conducted at a temperature within the range of from 450° to 600° C. for 0.5 to 1.0 sec. Supply of chlorine required for the reaction is effected at a single point of the reaction zone; the ratio between the reagents ensuring maximal yield of the desired products is defined by the formula: mole $Cl_2 = x$.mole $C_2H_6 + (x-1)$.mole $C_2H_4$, wherein $x = 1.9$ to $3.0$. For the removal of the heat evolved in the reaction use is made of chemically inactive diluents, such as hydrogen chloride, steam, nitrogen. The maximal yield of vinyl chloride is as high as 30% by weight. Therefore, commercial production of vinyl chloride by said prior art method is hindered mainly by the low yield of vinyl chloride and large amount of by-products.

The disadvantages of the prior art methods also include the ways in which the reaction temperature is controlled by means of the product recycle or admission of inert diluents into the reaction zone. The use of the product recycle involves increased power consumption for rectification, condensation, cooling and pumping of chloroethanes. The capital investment is also increased, since it is necessary to perform the stage of hydrochlorination of vinyl chloride to obtain an additional amount of 1,1-dichloroethane employed in the recycle.

The use of inert diluents for the process temperature control also increases power consumption for circulation and purification of said inert gases, while the use of steam necessitates corrosion-resistant process equipment, thus increasing capital investment. In the case of inert gases, due to an increased vapour tension of vinyl chloride, the product loss is increased owing to a natural entrainment thereof with the off-gases. This also necessitates larger capacities of purification units to avoid environmental pollution problems.

The present invention is aimed at overcoming the above-mentioned disadvantages.

It is an object of the present invention to provide a method of preparing vinyl chloride which will make it possible to increase the desired product yield.

Another object of the present invention is to provide a method of preparing vinyl chloride which can be carried out at lower power consumption rates.

These objects are accomplished by that in the preparation of vinyl chloride by way of chlorination of a gaseous mixture of ethane and ethylene at an elevated temperature, in accordance with the present invention, chlorinated is a gaseous mixture containing 5 to 50 vol.% of ethane and 50 to 95 vol.% of ethylene, and gaseous chlorine is supplied into the reaction zone in an amount defined by the formula: number of moles of chlorine $= 3m + 0.3n$, wherein m is the number of moles of ethane and n is the number of moles of ethylene, at 4 to 6 points evenly spaced along the reaction zone.

The method according to the present invention makes it possible to increase the yield of vinyl chloride up to 70% by weight with simultaneously reducing the power consumption 1.5 times as compared to the prior art method.

In accordance with the present invention, it is advisable to use, for the chlorination, a gaseous mixture comprising 30–35 vol.% of ethane and 65–70 vol.% of ethylene, which makes it possible to achieve a maximum yield of vinyl chloride, as high as 70% by weight. After separation of vinyl chloride a mixture of hydrogen chloride and ethylene remains, which may be utilized for the production of vinyl chloride by a prior art process comprising oxidative chlorination of ethylene and dehydrochlorination of 1,2-dichloroethane formed in the oxidative chlorination of ethylene. It is precisely with this composition of the starting products that the process may be performed completely balanced with respect to chlorine, i.e. without formation of any by-product hydrogen chloride.

To achieve a high process rate and complete conversion of chlorine and ethane, the chlorination according to the present invention should be preferably performed at a temperature ranging from 300° to 550° C.

An embodiment of the present invention resides in that the chlorination is conducted at a temperature of 450° C.; which enables complete conversion of chlorine and ethane at minimal formation of carbon black and resin.

In accordance with the present invention, it is also advisable that gaseous chlorine be supplied at different points of the reaction zone, in the following manner:
point 1—5 to 10 vol.% of chlorine
point 2—10 to 15 vol.% of chlorine
point 3—15 to 25 vol.% of chlorine,
points 4 to 6—the balance up to 100 vol.% of chlorine.

Owing to such supply of gaseous chlorine into the reaction zone, it is possible to lower power consumption for recycling the products and recovery thereof from the reaction mixture, as well as to reduce losses of vinyl chloride due to entrainment thereof.

These and other objects and advantages of the present invention will now become more fully apparent from the following detailed description of the method of preparing vinyl chloride and examples illustrating the same.

The method of preparing vinyl chloride according to the present invention is based on chlorination of a gaseous mixture of ethane and ethylene.

It is known that the process of chlorination of ethane may be represented by a combination of basic reactions:

beyond the abovementioned limits will result in a reduced yield of vinyl chloride and poorer economics of the process.

It has been found that upon chlorination of a gaseous mixture containing 30–35 vol.% of ethane and 65–70 vol.% of ethylene the highest yield of vinyl chloride is attained, whereas the use of the unreacted ethylene and hydrogen chloride according to the method of the present invention makes it possible to balance the process with respect to chlorine.

Preparation of vinyl chloride by the method according to the present invention may be performed in conventional sectioned reactors. In order to perform the process safely so as to avoid spontaneous combustion and resinification, it is advisable to exclude dilution of the reaction mixture with inert gases or the reaction products as in the prior art methods; the process should be performed in a flow-type reactor provided with inlet pipes for admission of chlorine, located over the entire length of the reactor shell. This makes it possible to substantially reduce power consumption for recycling of the products and recovery thereof from the reaction mixture as well as lower losses of vinyl chloride due to its being carried away. The best results are obtained with the supply of chlorine at least 4 points of the reaction zone evenly spaced over its length.

It has been found that said effective decrease in power consumption for recycling of the reaction products and recovery thereof from the reaction mixture as well as reduced losses of vinyl chloride may be achieved if the supply of gaseous chlorine at different points of the reaction zone is performed in the following manner: at point 1 located close to the inlet of the gaseous mixture of ethane and ethylene 5 to 10 vol.% of chlorine are supplied;
at point 2–10 to 15 vol.% of chlorine;
at point 3–15 to 25 vol.% of chlorine;
at points 4 to 6—the balance (i.e. the remaining amount of chlorine adding up to 100 vol.%), in equal portions.

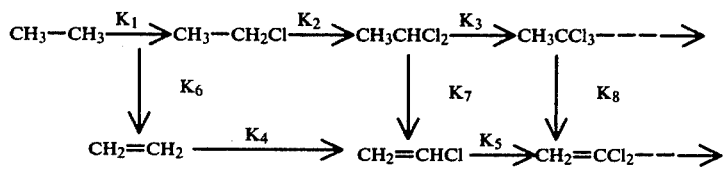

According to this scheme, vinyl chloride is formed from pyrolysis of 1,1-dichloroethane ($K_7$) and partly by chlorination of ethylene $K_4$) resulting from pyrolysis of chloroethyl. The formed vinyl chloride is further converted (according to the reaction $K_5$) to vinylidene chloride. This is achieved by admission, into the reaction zone, of large quantities of ethylene. Since the rate of chlorination of ethylene ($K_4$) is substantially higher than the rate of conversion of vinyl chloride to vinylidene chloride ($K_5$), a portion of chlorine which, in the case of using ethane has been consumed in the reaction $K_7$, now reacts with ethylene to form vinyl chloride. In this manner it is possible not only to increase the yield of vinyl chloride directly from ethane, but to obtain an additional amount of vinyl chloride as well as due to partial chlorination of ethylene.

In accordance with the present invention, subjected to chlorination is a gaseous mixture containing 5 to 50 vol.% of ethane and 50 to 95 vol.% of ethylene. An increased or decreased amount of ethane in the mixture In accordance with the present invention, gaseous chlorine should be supplied into the reaction zone in an amount defined by the formula: number of moles of chlorine-$=3m+0.3n$, wherein m is the number of moles of ethane and n is the number of moles of ethylene.

Meeting this requirement (along with others specified hereinabove) makes it possible to increase the yield of vinyl chloride up to 70% by weight and to reduce power consumption 1.5 times as compared to the prior art methods.

The recommended temperature of the chlorination process according to the present invention should range from 300° to 550° C., thus ensuring a high process rate; however, it has been found that, at a temperature of 450° C., complete conversion of ethane and chlorine is obtained at a minimum formation of resin and carbon black.

EXAMPLES 1 to 4

Chlorination of an ethane-ethylene mixture is effected at fixed rates of supply of ethane, ethylene and chlorine in a quartz reactor 40 cm long (volume of 70 cm$^3$) having four mixing means for admission of chlorine avenly spaced over the reaction zone length every 10 cm. The reactor is provided with an electric heating means and a device for automatic control of the process temperature with an accuracy of +1.5° C. The reaction products are analyzed by gas-liquid chromatography. In all experiments, the content of ethylene in the feed (starting) mixture is about 68% by volume. The supplied chlorine is distributed over the reactor length in the following manner: at point 1 (downstream with respect to admission of chlorine into the reactor) chlorine is supplied at a rate of 2 l/hr, at point 2, 3.5 l/hr, at point 3, 4.5 l/hr, and at point 4, 12 l/hr.

The test results are shown in Table 1 hereinbelow.

EXAMPLES 5 to 8

Into the reactor described in the foregoing Examples 1 to 4 chlorine is supplied at a rate of 22.0 l/hr along with an ethane-ethylene mixture containing 50% of ethylene fed at a rate of from 14.6 to 44 l/hr, thus ensuring chlorine-to-ethane ratio within the range of from 1.0 to 3.0. The reaction temperature is maintained equal to 400°+1.5° C.

The contact time is 1.5 to 5.0 seconds. Distribution of the supplied chlorine over the reaction zone length is similar to that described in Examples 1 to 4 hereinabove. The reaction products are analyzed chromatographically. The test results are shown in Table 2 hereinbelow.

EXAMPLES 9-10

Subjected to chlorination is an ethane-ethylene mixture containing 70 vol.% of ethylene at the temperature of 450°+1.5° C. for 1.5-2.0 sec. The ratio between chlorine and ethane is 2.75 and 3.3. In this series of experiments use is made of the reactor described in Examples 1 to 4 hereinbefore. The chlorine supplied into the reactor is distributed over the reaction zone length in the following manner (mol. percent of the total amount):

point 1—10;
point 2—15;
point 3—25;
point 4—50.

The composition of the reaction products is determined chromatographically.

The results of the experiments are shown in Table 3 hereinbelow.

EXAMPLES 11-12 (comparative)

In a reactor similar to that described in Examples 1 to 4 hereinbefore pure ethane or pure ethylene is chlorinated under conditions ensuring a maximum yield of vinyl chloride.

The test results are shown in Table 4 hereinbelow.

As follows from the above Examples, the method according to the present invention ensures a higher yield of vinyl chloride up to 72% by weight (see Table 3). The method of this invention also makes it possible to reduce power consumption and product losses.

Table 1

| Example No. | Amount of the reagent fed into the reactor, l/hr | | | Temperature, °C. | Composition of chlororganic products of the reaction, wt. % | | | | | | Degree of conversion % | | |
|---|---|---|---|---|---|---|---|---|---|---|---|---|---|
| | ethane | ethylene | chlorine | | Vinyl chloride | Chloroethyl | Vinylidene chloride | 1,1-dichloroethane | 1,1,1-trichloroethane | 1,2-dichloroethane | Chlorine | Ethane | Ethylene |
| 1 | 10.7 | 22.5 | 22.0 | 300 | 9,90 | 30,80 | — | 22.20 | 1.73 | 35.40 | 96.0 | 88.0 | 21.0 |
| 2 | 10.6 | 22.6 | 22.0 | 350 | 26.60 | 17.40 | 0.76 | 27.95 | 5.35 | 21.93 | 99.0 | 96.0 | 7.0 |
| 3 | 10.0 | 22.0 | 22.0 | 400 | 38.10 | 5.50 | 5.23 | 26.00 | 16.90 | 8.30 | 100.0 | 100.0 | 15.0 |
| 4 | 10.5 | 22.5 | 22.0 | 450 | 44.71 | 7.43 | 6.91 | 19.47 | 20.13 | 1.34 | 100.0 | 100.0 | 10.0 |

Table 2

| Example No. | Molar ratio chlorine:ethane | Composition of chlororganic products of the reaction, wt.% | | | | | | | | | conversion degree, % | | |
|---|---|---|---|---|---|---|---|---|---|---|---|---|---|
| | | Vinyl chloride | Chloroethyl | Vinylidene chloride | Dichloroethylenes | 1,1-dichloroethane | 1,1,1-trichloroethane | 1,2-dichloroethane | Perchloroethylene | 1,1,2 trichloroethane | Tetrachloroethane | Chlorine | Ethylene | Ethane |
| 5 | 1.0 | 3.96 | 69.4 | — | — | 29,86 | 0.68 | 4.39 | 0.34 | 0.10 | 0.29 | 100.8 | — | 76.5 |
| 6 | 2.0 | 44.0 | 0.78 | 11.85 | 0.12 | 12.50 | 26.80 | 3.05 | 0.24 | 0.66 | — | 99.1 | 24.5 | 100.0 |
| 7 | 2.5 | 48.6 | — | 24.20 | 0.94 | 2.24 | 17.33 | 4.95 | 0.21 | 1.10 | 0.42 | 98.5 | 21.7 | 100.0 |
| 8 | 3.0 | 50.7 | — | 23.20 | 1.63 | 1.42 | 17.25 | 4.88 | — | 0.92 | — | 95.0 | 20.0 | 100.0 |

Table 3

| Example No. | Molar ratio chlorine:ethane | Composition of chlororganic products of the reaction, Wt.% | | | | | | | | | | Degree of conversion, % | | |
|---|---|---|---|---|---|---|---|---|---|---|---|---|---|---|
| | | Vinyl chloride | Chloroethyl | Vinylidene chloride | Dichloroethylenes | 1,1-dichloroethane | 1,1,1-trichloroethane | 1,2-dichloroethane | Perchloroethylene | 1,1,2-trichloroethane | Tetrachloroethane | Chlorine | Ethylene | Ethane |
| 9 | 2.75 | 61.40 | 4.62 | 6.12 | | 10.58 | 14.58 | 2.7 | — | — | — | 100.0 | 21.0 | 100.0 |

Table 3-continued

| Example No. | Molar ratio chlorine:ethane | Composition of chlororganic products of the reaction, Wt.% | | | | | | | | | Degree of conversion, % | | |
|---|---|---|---|---|---|---|---|---|---|---|---|---|---|
| | | Vinyl chloride | Chloroethyl | Vinylidene chloride | Dichloroethylenes | 1,1-dichloroethane | 1,1,1-trichloroethane | 1,2-dichloroethane | Perchloroethylene | 1,1,2-trichloroethane | Tetrachloroethane | Chlorine | Ethylene | Ethane |
| 10 | 3.3 | 71.72 | 1.58 | 9.86 | | 5.77 | 9.10 | 2.02 | — | — | 0.6 | 100.0 | 25.0 | 100.0 |

Table 4

| Example No. | Hydrocarbon | Temperature, °C | Ratio (molar) chlorine:hydrocarbon | Composition of chlororganic products of the reaction, wt. % | | | | | | | | | | | Degree of conversion, % | |
|---|---|---|---|---|---|---|---|---|---|---|---|---|---|---|---|---|
| | | | | Vinyl chloride | Chloroethyl | Vinylidene chloride | Dichloroethylenes | 1,1-dichloroethane | 1,1,1-trichloroethane | 1,2-dichloroethane | Trichloroethylene | 1,1,2-trichloroethane | Perchloroethane | Tetrachloroethane | Chlorine | Hydrocarbon |
| 11 | Ethane | 400 | 2,4 | 32,20 | 5,55 | 19,00 | — | 12.00 | 27.00 | 2.90 | 0.65 | 0.70 | — | — | 91,5 | 100.0 |
| 12 | Ethylene | 400 | 1,0 | 57,60 | — | 19,15 | 8,32 | — | — | 5.98 | — | 3.66 | 0.36 | 4.88 | 97,5 | 93.0 |

What is claimed is:

1. A method of preparing vinyl chloride comprising thermal chlorination of a gaseous mixture containing 5 to 50 vol.% of ethane and 50 to 95 vol.% of ethylene, by means of gaseous chlorine supplied into the reaction zone in an amount defined by the formula: amount of chlorine moles=3m+0.3n, wherein m is the number of moles of ethane, n is the number of moles of ethylene, said gaseous chlorine being supplied at 4–6 points of said reaction zone evenly distributed along the length thereof.

2. A method of preparing vinyl chloride according to claim 1, wherein chlorinated is a gaseous mixture containing 30 to 35 vol.% of ethane and 65 to 70 vol.% of ethylene.

3. A method of preparing vinyl chloride according to claim 1, wherein said chlorination is conducted at a temperature within the range of from 300° to 550° C.

4. A method of preparing vinyl chloride according to claim 1, wherein said chlorination is conducted at a temperature of 450° C.

5. A method of preparing vinyl chloride according to claim 1, wherein said supply of gaseous chlorine at different points of the reaction zone is effected in the following manner: point 1 5 to 10 vol.% of chlorine
point 2—10 to 15 vol.% of chlorine
point 3—15 to 25 vol.% of chlorine
points 4 to 6—the balance.

* * * * *